(12) United States Patent
Jetten et al.

(10) Patent No.: US 7,615,137 B2
(45) Date of Patent: *Nov. 10, 2009

(54) PROCESS FOR RECOVERING CAPROLACTAM FROM AQUEOUS CAPROLACTAM PRODUCT USING IN SITU PREPARED ALKALI AMINO CAPROATE

(75) Inventors: Arnold G M Jetten, Moorveld (NL); Nicolaas F Haasen, Limbricht (NL); Gerardus W A Hangx, Weert (NL)

(73) Assignee: DSM IP Assets B.V., Heerlen (NL)

( * ) Notice: Subject to any disclaimer, the term of this patent is extended or adjusted under 35 U.S.C. 154(b) by 729 days.

This patent is subject to a terminal disclaimer.

(21) Appl. No.: 10/486,727

(22) PCT Filed: Aug. 23, 2002

(86) PCT No.: PCT/NL02/00559

§ 371 (c)(1),
(2), (4) Date: Sep. 3, 2004

(87) PCT Pub. No.: WO03/018550

PCT Pub. Date: Mar. 6, 2003

(65) Prior Publication Data

US 2005/0011744 A1    Jan. 20, 2005

(30) Foreign Application Priority Data

Aug. 27, 2001 (EP) ................................. 01203214
Aug. 27, 2001 (EP) ................................. 01203215
Aug. 27, 2001 (EP) ................................. 01203217

(51) Int. Cl.
*B01D 3/34* (2006.01)
*C07D 201/16* (2006.01)

(52) U.S. Cl. .......................... 203/37; 159/47.1; 203/14; 203/29; 203/91; 540/540

(58) Field of Classification Search .................. 203/1, 203/14, 29, 37, 91; 159/47.1; 540/540
See application file for complete search history.

(56) References Cited

U.S. PATENT DOCUMENTS

| 4,720,328 | A | * | 1/1988 | Corbin et al. ................. 203/37 |
| 4,892,624 | A | * | 1/1990 | Fuchs ........................... 203/37 |
| 5,496,941 | A | | 3/1996 | Ritz et al. |
| 5,700,358 | A | * | 12/1997 | Fuchs et al. .................. 203/31 |
| 2005/0029086 | A1 | * | 2/2005 | Groot Zevert et al. ......... 203/37 |

FOREIGN PATENT DOCUMENTS

DE    202 870    10/1983

OTHER PUBLICATIONS

Publication 1: Japanese Patent Application Laid-Open No. 7-330720, Dec. 19, 1995 (D1).
Publication 2: Kagaku Jiten by Tokyo Kagaku Dojin, 3$^{rd}$ Ed., Oct. 1, 2994 (D2).

* cited by examiner

*Primary Examiner*—Virginia Manoharan
(74) *Attorney, Agent, or Firm*—Nixon & Vanderhye P.C.

(57) ABSTRACT

A continuous process is provided for recovering caprolactam from aqueous caprolactam product which includes (i) caprolactam, (ii) impurities, and (iii) water by (a) adding alkali hydroxide to the aqueous caprolactam product, in an amount of not more than 100 mmol alkali hydroxide per kg of caprolactam; (b) reacting at least part of the added alkali hydroxide to form alkali amino caproate, to obtain a caproate-enriched caprolactam product; and (c) distilling the caproate-enriched caprolactam product at reduced pressure.

16 Claims, No Drawings

PROCESS FOR RECOVERING CAPROLACTAM FROM AQUEOUS CAPROLACTAM PRODUCT USING IN SITU PREPARED ALKALI AMINO CAPROATE

CROSS REFERENCE TO RELATED APPLICATION

This application is the National Phase of International Application PCT/NL02/00559 filed Aug. 23, 2002 which designated the U.S., and that International Application was published under PCT Article 21(2) in English.

The invention relates to a process for recovering caprolactam from aqueous caprolactam product.

The production of caprolactam often comprises the preparation of aqueous caprolactam product and the purification of such aqueous caprolactam product. The purification can include distillation at reduced pressure to separate out low-boiling and/or high boiling organic compounds. It is known that such distillation can be effected in the presence of a base. As a base sodium hydroxide is generally used, see for instance U.S. Pat. No. 4,457,807, U.S. Pat. No. 5,496,941, U.S. Pat. No. 3,893,324, and U.S. Pat. No. 3,792,045. When hydroxide enters the distillation column in which the distillation. is effected, oligomerization and/or polymerization of the caprolactam can occur which is disadvantageous since it often results in fouling of the distillation equipment. DD-A-202870 describes that the use of alkali amino caproate instead of alkali hydroxide diminishes the occurrence of polymerization, and, consequently the occurrence of fouling of the distillation equipment. In the process of DD-A-202870 a solution comprising 37.4 wt. % alkali amino caproate is prepared in a separate reaction vessel by reacting the corresponding alkali hydroxide with raw caprolactam at a temperature of 80° C. for 10 hours. After completion of the reaction, the alkali amino caproate-containing solution is introduced into the aqueous caprolactam product to be purified, after which the distillation is effected.

In the process according to DD-A-202870 an extra process step is used for the preparation of the alkali amino caproate. This is in particular disadvantageous when the process is to be carried out continuously.

Goal of the invention is to solve to provide a process wherein no additional step for the preparation of the alkali amino caproate is necessary.

This goal is achieved according to the invention by providing a continuous process for recovering caprolactam from aqueous caprolactam product, said aqueous caprolactam product comprising (i) caprolactam, (ii) impurities, and (iii) water, said process comprising:

adding alkali hydroxide to the aqueous caprolactam product, in an amount of not more than 100 mmol alkali hydroxide per kg of caprolactam;

reacting at least part of the added alkali hydroxide to form alkali amino caproate, to obtain a caproate-enriched caprolactam product; and distilling the caproate-enriched caprolactam product at reduced pressure.

According to the invention a simple process is provided wherein alkali amino caproate is formed in situ.

According to the invention at least part of the added alkali hydroxide is reacted to form alkali amino caproate prior to distilling the caproate-enriched caprolactam product. Preferably, at least 50 mol. %, more preferably at least 75 mol. %, in particular at least 85 mol. %, more in particular at least 90 mol. %, most preferably substantially all of the added alkali hydroxide is reacted to form alkali amino caproate prior to distilling the caproate-enriched caprolactam product. In a process which comprises feeding the caproate-enriched caprolactam product to a distillation zone, and distilling the caproate-enriched caprolactam product in said distillation zone, this is to be understood to mean that at least part, preferably at least 50 mol. %, more preferably at least 75 mol. %, in particular at least 85 mol. %, more in particular at least 90 mol. %, most preferably substantially all of the added alkali hydroxide is reacted to form alkali amino caproate prior to feeding the caproate-enriched caprolactam product to the distillation zone. Increasing the conversion of the reaction has the advantage that the extent of oligomerization/polymerization during the distillation under reduced pressure is lessened.

The reaction of the added alkali hydroxide to form the alkali amino caproate can be effected by applying a suitable residence time, said residence time being dependent on the temperature and concentrations in the aqueous caprolactam product. A suitable residence time can be determined by the skilled person. Generally, the residence time is at least 30 minutes, preferably at least 60 minutes. As used herein the residence time refers to the period between the addition of the alkali hydroxide to the aqueous caprolactam product and the start of the distillation. In a process which comprises feeding the caproate-enriched caprolactam product to a distillation zone, and distilling the caproate-enriched caprolactam product in said distillation zone, this is to be understood to mean that the residence time refers to the period between the addition of the alkali hydroxide to the aqueous caprolactam product and the feeding of the caproate-enriched caprolactam product to the distillation zone.

Advantageously, the process comprises purifying the aqueous caprolactam product in one or more steps after said adding and prior to the distillation at reduced pressure. Preferably, said one or more steps include the separation of water by evaporation.

Advantageously, the aqueous caprolactam product is added to a buffer tank which may be present in the process and the alkali hydroxide is added to the aqueous caprolactam product in a buffer tank or prior to feeding the aqueous caprolactam product to a buffer tank. This has the advantage that the residence time is increased.

The aqueous caprolactam product comprises (i) caprolactam, (ii) impurities, and (iii) water. Typically, the aqueous caprolactam product comprises 15 to 99.9 wt. % of caprolactam, in particular at least 50 wt. % of caprolactam, more in particular at least 75 wt. % of caprolactam. Preferably, the aqueous caprolactam product comprises at least 3 wt. % of water, more preferably at least 5 wt. % of water. Typically the sum quantity of water and caprolactam in the caprolactam product is preferably at least 95 wt. %, in particular at least 97 wt. %, more in particular at least 98 wt. %. The above percentages are given relative to the weight of the aqueous caprolactam product. The impurities may be any organic impurities, e.g. low-boiling organic impurities (having a lower boiling point than caprolactam) and/or high-boiling organic impurities (having a higher boiling point than caprolactam).

The caproate-enriched caprolactam product comprises caprolactam. Typically, the caproate-enriched caprolactam product comprises 95 to 99.9 wt. % of caprolactam, in particular at least 97 wt. % of caprolactam, more in particular at least 98 wt. % of caprolactam (relative to the weight of caproate-enriched caprolactam product).

The caproate-enriched caprolactam product may include water. Preferably, the caproate-enriched caprolactam product comprises less than 5 wt. % of water, more preferably less than 3 wt. %, in particular less than 2 wt. %, more in particular less than 1 wt. % (relative to the weight of caproate-enriched caprolactam). A lower amount of water has the advantage that a reduced pressure during distilling is easier to create and maintain.

The caproate-enriched caprolactam product has a higher concentration of alkali amino caproate (expressed as mol of alkali amino caproate per kg of caprolactam) than the aqueous caprolactam product. Preferably, at least 50 mol. % of the bases selected from the group consisting of alkali hydroxide and alkali amino caproate in the caproate-enriched caprolactam product entering the distillation zone is present as alkali amino caproate, more preferably at least 75 mol. %, in particular at least 85 mol. %, more in particular at least 90 mol. %, most preferably substantially all of said bases. Increasing the relative amounts of alkali amino caproate has the advantage that the occurrence of oligomerization/polymerization is lessened.

As used herein all concentrations mentioned for the caproate-enriched caprolactam product refer to the concentrations in the caproate-enriched caprolactam product prior to distilling the caproate-enriched caprolactam product. In a process which comprises feeding the caproate-enriched caprolactam product to a distillation zone, and distilling the caproate-enriched caprolactam product in said distillation zone, this is to be understood to mean that all concentrations mentioned for the caproate-enriched caprolactam product refer to the concentrations in the caproate-enriched caprolactam product entering the distillation zone.

In an embodiment, the process is a continuous process for recovering caprolactam from aqueous caprolactam product, said aqueous caprolactam product comprising (i) caprolactam, (ii) impurities, and (iii) water, said process comprising:
continuously adding alkali hydroxide to a stream of the aqueous caprolactam product
reacting at least part of the added alkali hydroxide to form alkali amino caproate to obtain a stream of caproate-enriched caprolactam product,
continuously feeding the stream of the caproate-enriched caprolactam product to a distillation zone
in said distillation zone, distilling the caproate-enriched caprolactam product at reduced pressure.

In this embodiment the alkali hydroxide can be added to the stream of aqueous caprolactam product at any suitable point. Suitable points include points which are chosen such that the residence time of the added alkali hydroxide in the aqueous caprolactam stream is sufficiently long to effect the reaction prior to feeding the caproate-enriched caprolactam product to the distillation zone. The residence time is generally dependent on the conditions in the stream, for instance on the composition and the temperature.

According to the invention not more than 100 mmol alkali hydroxide is added per kg of caprolactam. It is possible to add less than 50 mmol alkali hydroxide per kg of caprolactam, for instance less than 20 mmol per kg of caprolactam. In an embodiment, the process comprises adding between 0.05 and 10 mmol of the alkali hydroxide per kg of caprolactam, preferably between 0.05 and 5.0 mmol per kg, more preferably between 0.10 and 4.5 mmol per kg, in particular between 0.15 and 3.0 mmol per kg, more in particular between 0.20 and 2.0 mmol, most preferably less than 1.0 mmol alkali hydroxide per kg of caprolactam. Decreasing the amount of added alkali hydroxide to below the preferred upper limits has the advantage that the PAN number is decreased. Increasing the amount of added alkali hydroxide to above the preferred lower limits has the advantage that the occurrence of undesired fluctuation in quality, e.g. resulting from the oxidation of caprolactam during distillation, is decreased.

In a preferred embodiment the caproate-enriched caprolactam product is an alkaline caprolactam product having an alkalinity of less than 5 meq. (5 milliequivalent) per kg of caprolactam. This has the advantage that purified caprolactam is obtained having a high quality, in particular a low PAN number (as determined in accordance with ISO DIS 8660—Plastics-Determination of permanganate index of caprolactame-Spectometric method, revision of first edition (ISO 8660; 1988)). Moreover a low value for the extinction (as determined in accordance with ISO 7059—caprolactam for industrial use—Determination of absorbance at a wavelength of 290 nm) is obtained.

As used herein alkalinity refers to the alkalinity at a temperature of 25° C. as determined by titration (after diluting the alkaline caprolactam product with water of pH=5.7 to obtain a solution containing 15 wt. % caprolactam) with a 0.01 N HCl solution to a pH of 5.7, whereby $$\text{alkalinity} = \frac{v*t}{a*0.15}*1000$$

Where:
v=ml of HCl solution added
t=molarity of HCl solution (=0.01)
a=weight of sample (g)

Preferably, the alkalinity of the caproate-enriched caprolactam product is lower than 4.5 meq. per kg of caproate-enriched caprolactam product, more preferably lower than 4.0 meq. per kg in particular lower than 3.0 meq. per kg, more in particular lower than 2.0 meq. per kg, most preferably lower than 1.0 meq. per kg. This further decreases the PAN number.

Preferably, the alkalinity of the caproate-enriched caprolactam product is higher than 0.05 meq. per kg of caproate-enriched caprolactam product, more preferably higher than 0.10 meq. per kg, in particular higher than 0.15 meq. per kg. Increasing the alkalinity to above these values improves the stability, i.e. the sensitivity to occurrence of undesired fluctuations in quality.

As used herein the values mentioned for the alkalinity and concentrations in the caproate-enriched caprolactam product refer to the values of the caproate-enriched caprolactam product prior to distilling. In a process which comprises feeding the caproate-enriched caprolactam product to a distillation zone, and distilling the caproate-enriched caprolactam product in said distillation zone, this is to be understood to mean that all mentioned values for the alkalinity for the caproate-enriched caprolactam product refer to the concentrations in the caproate-enriched caprolactam product entering the distillation zone.

In a possible embodiment of the invention, the aqueous caprolactam product to which the alkali hydroxide is added has an acidity of between 0 and 5 meq. per kg caprolactam, is neutral, or has an alkalinity of between 0 and 5 meq. per kg caprolactam. In this embodiment caproate-enriched caprolactam product having the preferred alkalinity can be prepared using only very small amounts of alkali hydroxide. As used herein acidity refers to the acidity at a temperature of 25° C. as determined by titration (after diluting the alkaline caprolactam product with water of pH=5.7 to obtain a solution containing 15 wt. % caprolactam) with a 0.01 N NaOH solution to a pH of 5.7, whereby $$\text{acidity} = \frac{v*t}{a*0.15}*1000$$

Where:

v=ml of NaOH solution added t=molarity of NaOH solution (=0.01)

a=weight of sample (g)

Preferably, the aqueous caprolactam product to which the alkali hydroxide is added is neutral or has an alkalinity of between 0 and 5 meq. per kg of caprolactam. Preferably, the amount of added alkali hydroxide is decreased when the caprolactam product is less acidic/more alkaline.

Preferably, the alkali hydroxide is selected from the group consisting of sodium hydroxide and potassium hydroxide. Preferably, the alkali hydroxide is sodium hydroxide.

The aqueous caprolactam product may be obtained in various ways. A Beckmann rearrangement of cyclohexanone oxime may be effected in the presence of sulphuric acid or oleum, resulting in a Beckmann rearrangement mixture. A base, preferably ammonia, may be added to the Beckmann rearrangement mixture, resulting in a neutralized Beckmann rearrangement mixture. In one embodiment of the invention the preparation of the caprolactam product includes, (a) recovering from a neutralized Beckmann rearrangement mixture, by extraction with an organic solvent, an organic product comprising the organic solvent and caprolactam, (b) recovering from said organic product, by extraction with water or by evaporation of the organic solvent in the presence of water, an aqueous caprolactam product. Following its recovery from the organic product, the aqueous caprolactam product is preferably hydrogenated in the presence of a hydrogenation catalyst. In the event that the aqueous caprolactam product is recovered from the organic product by evaporation of the organic solvent in the presence of water, the organic product is preferably washed with water or with an alkaline aqueous solution prior to said evaporation. In the event that the aqueous caprolactam product is recovered from the organic product by extraction with water, the aqueous caprolactam product is preferably subjected to a ion exchanger prior to hydrogenation. Preferably, said alkali hydroxide is added to the aqueous caprolactam product after a hydrogenation step.

The distillation may be carried out in any suitable distillation zone, for instance a distillation column. The distillation is effected at reduced pressure. Preferably the distillation is effected at a pressure of less than 50 kPa, more preferably less than 20 kPa, in particular less than 10 kPa. Preferably, the temperature is between 100 and 200° C., more preferably between 110 and 180° C. These temperatures refer to the temperature in the bottom of the distillation column in which the distillation is effected. Typically, the distilling includes separating low-boiling organic impurities (having a lower boiling point than caprolactam) from the caproate-enriched caprolactam product and/or separating organic high-boiling impurities (having a higher boiling point than caprolactam) from the caproate-enriched caprolactam product. Preferably, the distilling includes, in a first step, separating out as a top product low-boiling impurities from the alkaline caproate-enriched caprolactam product while leaving caproate-enriched caprolactam product containing high-boiling impurities as a bottom product, and, in a second step, separating out high-boiling impurities from the bottom product, and recovering purified caprolactam as a top product.

Preferably, the caprolactam is ε-caprolactam.

The invention will now be elucidated with reference to the following example without, however, being limited thereto.

COMPARATIVE EXPERIMENT AND EXAMPLE I

In a continuous process for the production of pure ε-caprolactam, a stream of caprolactam product was continuously produced by Beckmann rearrangement of cyclohexanone oxime in the presence of oleum, neutralizing the Beckmann rearrangement mixture with ammonia, separating caprolactam from the neutralized Beckmann rearrangement by extraction techniques. Said stream was subjected to a series of purification steps including purification with an ion exchanger, hydrogenation and a first dewatering. The resulting stream of aqueous caprolactam product contained about 85 wt. % caprolactam, about 15 wt. % water, and impurities. This stream was dewatered in a series of evaporators, the temperatures in the evaporators varying between 80 and 125° C. The total residence in the evaporators (including the residence time in the piping between the evaporators) was 3 hours. As a result, caprolactam product was obtained containing about 0.5 wt. % water. The stream of caprolactam product leaving the series of evaporators was distilled in two steps under reduced pressure. In the first step low-boiling impurities and water were separated in a distillation column, at a (bottom) temperature of 175° C., and a pressure of 5.2 kPa, the residence time being several minutes. In the second step high-boiling impurities were separated in a distillation column at a (bottom) temperature of 133° C., a pressure of 1.2 kPa, the residence time being 1 hour.

Now it is shown how the skilled person can determine at which points the sodium hydroxide can be added to the stream of aqueous caprolactam product to achieve sufficient formation of sodium amino caproate prior to feeding said stream to the first distillation column of the distillation at reduced pressure.

In a first experiment (a 15 wt. % aqueous solution of NaOH) (Comparative Experiment) was continuously added to the stream leaving the series of evaporators. Per kg of caprolactam 5 mmol of NaOH was added. Analysing (e.g. by titration) the stream just before entering the first distillation column reveals that the stream still contains considerably amounts of NaOH. In the distillation residue of the second distillation step, 8.7 wt. % of solids (polymerization products) are found.

In a second experiment (example I) a same amount of NaOH is added to the stream of aqueous caprolactam which is fed to the series of evaporators (containing 15 wt. % of water). In the stream entering the first distillation column at least 90 wt. % of the added NaOH appears to have been reacted to sodium amino caproate. In the residue of the second distillation step under reduced pressure no oligomers or polymers are found. Purified caprolactam meeting the required specifications is obtained.

This example (second experiment) shows that polymerization can be avoided without preparing alkali amino caproate in separate equipment.

EXAMPLES II-IX

Example I was repeated, whereby the sodium hydroxide was added to the stream of aqueous caprolactam product containing about 85 wt. % caprolactam, about 15 wt. % water, and impurities (the stream which is fed to the series of evaporators), said stream having the following specifications (PAN=2.6, $E_{290}$=0.32, VB=0.44 meq/kg, alkalinity=0.02 meq/kg). The amount of added NaOH was varied (see table 1). The specifications of the caprolactam obtained after distillation are indicated in table 1.

TABLE 1

| Example Nr. | Added NaOH mmol NaOH/ kg capr | Alkalinity feed First distillation (175° C.) step meq OH–/kg | PAN | $E_{290}$ | VB meq OH⁻/kg | Alkalinity meq OH⁻/kg |
|---|---|---|---|---|---|---|
| II | 4.80 | 4.83 | 3.71 | 0.14 | 0.16 | 0.012 |
| III | 2.90 | 2.92 | 3.60 | 0.13 | 0.14 | 0.015 |
| IV | 1.25 | 1.29 | 3.54 | 0.13 | 0.11 | 0.017 |
| V | 0.90 | 0.95 | 2.88 | 0.11 | 0.12 | 0.013 |
| VI | 0.75 | 0.78 | 2.89 | 0.12 | 0.18 | 0.012 |
| VII | 0.60 | 0.65 | 2.59 | 0.12 | 0.12 | 0.011 |
| VIII | 0.50 | 0.55 | 1.15 | 0.06 | 0.11 | 0.024 |
| IX | 0.30 | 0.32 | 1.26 | 0.07 | 0.17 | 0.023 |

The specifications given were determined as follows:
PAN: ISO DIS 8660—Plastics-Determination of permanganate index of caprolactam-Spectrometric method, revision of first edition ISO 8660; 1988,
E290: ISO 7059—caprolactam for industrial use—determination of absorbance at a wavelength of 290 nm,
Volatile bases (VB) ISO 8661—Caprolactam for industrial use—Determination of volatile bases content—Titrimetric method after distillation.
Alkalinity: titration with a 0.01 molar aqueous solution of hydrochloric acid to a pH of 5.73.

These examples show that the PAN number is decreased without impairing the other properties of the caprolactam, if the amount of added NaOH is decreased. Moreover the extinction decreases with decreasing amount of added NaOH.

The invention claimed is:

1. A continuous process for recovering caprolactam from an aqueous caprolactam product comprising the steps of:
   (a) providing an aqueous caprolactam product comprised of (i) caprolactam, (ii) impurities, and (iii) water obtained by Beckmann rearrangement of cyclohexanone oxime;
   (b) continuously adding alkali hydroxide to the aqueous caprolactam product in an amount between 0.05 and 5.0 mmol alkali hydroxide per kg of caprolactam;
   (c) allowing at least 50 mol. % of the alkali hydroxide continuously added to the aqueous caprolactam product according to step (b) to react so as to form alkali amino caproate in situ within the aqueous caprolactam product and thereby obtain a caproate-enriched caprolactam product comprised of (i) caprolactam, (ii) impurities, (iii) alkali amino caproate, and optionally (iv) water; and
   (d) continuously introducing the caproate-enriched caprolactam product to a distillation zone and distilling the caproate-enriched caprolactam product in the distillation zone at reduced pressure so as to obtain purified caprolactam therefrom.

2. Process according to claim 1, wherein step (c) comprises reacting at least 75 mol. % of the added alkali hydroxide to form alkali amino caproate in situ within the aqueous caprolactam product prior to said distilling step (d).

3. Process according to claim 1, wherein the residence time of the added alkali hydroxide according to step (c) is sufficiently long so as to effect reaction to form the alkali amino caproate prior to the distilling step (d).

4. Process according to claim 3, wherein said residence time is at least 30 minutes.

5. Process according to claim 1, wherein the aqueous caprolactam product to which the alkali hydroxide is added comprises at least 15 wt. % of caprolactam and at least 3 wt. % of water.

6. Process according to claim 1, wherein the caproate-enriched caprolactam product comprises at least 95 wt. % of caprolactam.

7. Process according to claim 1, wherein the caproate-enriched caprolactam product comprises less than 2 wt. % of water.

8. Process according to claim 1, wherein the process comprises purifying the aqueous caprolactam product in at least one purifying step practiced after step (b) and prior to step (d).

9. Process according to claim 8, wherein the at least one purifying step includes separating water from the aqueous caprolactam product by evaporation.

10. Process according to claim 1, wherein the distilling step (d) is effected at a temperature between 100 and 200° C.

11. Process according to claim 1, wherein the distilling step (d) is effected at a pressure of less than 10 kPa.

12. Process according to claim 1, wherein the distilling step (d) includes at least one of (d1) separating out low-boiling impurities from the caproate-enriched caprolactam product, and (d2) separating out high-boiling impurities from the caproate-enriched caprolactam product.

13. Process according to claim 12, wherein the distilling step (d) includes, in a first step (d1), separating out as a top product low-boiling impurities from the caproate-enriched caprolactam while leaving caprolactam product containing high-boiling impurities as a bottom product, and, in a second step (d2), separating out high-boiling impurities from the bottom product, and (d3) recovering caprolactam as a top product.

14. Process according to claim 1, wherein step (b) is practiced by adding the alkali hydroxide to a stream of the aqueous caprolactam product at a point which is chosen such that the residence time of the added alkali hydroxide in the stream is sufficiently long such as to effect reaction of said at least part of the added alkali hydroxide prior to distilling the caproate-enriched caprolactam product according to step (d).

15. Process according to claim 1, wherein step (c) comprises reacting at least 90 mol. % of the added alkali hydroxide to form alkali amino caproate in situ within the aqueous caprolactam product prior to said distilling step (d).

16. Process according to claim 1, wherein step (c) comprises reacting substantially all of the added alkali hydroxide to form alkali amino caproate in situ within the aqueous caprolactam product prior to said distilling step (d).

* * * * *